United States Patent
Van Zee

(10) Patent No.: US 10,779,495 B2
(45) Date of Patent: Sep. 22, 2020

(54) LETTUCE VARIETY NUN 09127 LTL

(71) Applicant: NUNHEMS B.V., Nunhem (NL)

(72) Inventor: Johan Engelbert Van Zee, Zaltbommel (NL)

(73) Assignee: NUNHEMS B.V., Nunhem (NL)

( * ) Notice: Subject to any disclaimer, the term of this patent is extended or adjusted under 35 U.S.C. 154(b) by 80 days.

(21) Appl. No.: 16/108,777

(22) Filed: Aug. 22, 2018

(65) Prior Publication Data

US 2018/0359979 A1 Dec. 20, 2018

Related U.S. Application Data

(60) Provisional application No. 62/549,542, filed on Aug. 24, 2017.

(51) Int. Cl.
*A01H 6/14* (2018.01)
*A01H 5/12* (2018.01)

(52) U.S. Cl.
CPC ............. *A01H 6/1472* (2018.05); *A01H 5/12* (2013.01)

(58) Field of Classification Search
None
See application file for complete search history.

(56) References Cited

U.S. PATENT DOCUMENTS

| | | | | |
|---|---|---|---|---|
| 9,491,923 | B2 * | 11/2016 | Munoz Munoz | A23K 10/30 |
| 2008/0222949 | A1 | 9/2008 | Bissonnette et al. | |
| 2013/0219544 | A1 * | 8/2013 | van Zee | A01H 5/12 800/265 |
| 2013/0247244 | A1 * | 9/2013 | Van Zee | A01H 5/12 800/265 |
| 2015/0126380 | A1 | 5/2015 | Van Dun | |
| 2016/0255799 | A1 * | 9/2016 | Bellec | A01H 5/12 |
| 2018/0255722 | A1 * | 9/2018 | Van Zee | A01H 5/12 |

FOREIGN PATENT DOCUMENTS

EP   1 197 137 A1   4/2002

OTHER PUBLICATIONS

Gonai, T., et. al., "Abscisic Acid in the Thermoinhibition of Lettuce Seed Germination and Enhancement of its Catabolism by Gibberellin", Journal of Experimental Botany, 2004, vol. 55, (394), pp. 111-118.

Martin, E., et al., "Identification of Markers Linked to Agronomic Traits in Globe Artichoke", Australian Journal of Crop Science, 2008, vol. 1, No. 2, pp. 43-46.

Needleman, S.B., et al., "A General Method Applicable to the Search for Similarities in the Amino Acid Sequence of Two Proteins", Journal of Molecular Biology, 1970, vol. 48, (3), pp. 443-453.

Nikolova, V., et al., "Diploidization of Cucumber (*Cucumis sativus* L.) Haploids by Colchini Treatment", Acta Societas Botanicorum Poloniae, 1996, vol. 65, pp. 311-317.

Parvathaneni, R.K., et al., "Fingerprinting in Cucumber and Melon (*Cucumis* spp.) Genotypes Using Morphological and ISSR Markers", J. Crop Sci. Biotech., 2011, (Mar.), vol. 14, No. 1, pp. 39-43.

Rice, P., et al., "EMBOSS: The European Molecular Biology Open Software Suite", Trends in Genetics, 2000, vol. 16, Issue 6. pp. 276-277.

Smith, R., et al., "Leaf Lettuce Production in California", Publication 7216, 2011, http:anrcatalog.ucanr.edu/pdf/7216.pdf.

Teng, W., et al., "Rapid Regeneration of Lettuce from Suspension Culture", HortScience, 1992, vol. 27, No. 9, pp. 1030-1032.

Teng, W., et al., "Regenerating Lettuce from Suspension Culture in a 2-Liter Bioreactor", HortScience, 1993, vol. 28, No. 6, pp. 669-671.

Turini, T., et al., "Iceberg Lettuce Production in California", Publication 7215, 2011, http:anrcatalog.ucanr.edu/pdf/7215.pdf.

UPOV, "Guidelines for the Conduct of Tests for Distinctness, Uniformity and Stability", TG'/013/11 (Geneva 2006, last updated Apr. 5, 2017).

USDA Department of Agriculture, Agriculture Marketing Service, "Objective description of Variety—Lettuce (*Lactuca sativa* L.)", 2015, ams.usda.gov/ undersites/default/files/media/01-Lettuce%20ST-470-01%202015.pdf.

Vidavsky F., et. al., "Tomato Breeding Lines Resistant and Tolerant to Tomato Yellow Leaf Curl Virus Issued from Lycopersicon hirsutum", Phytopathology, 1998, vol. 88, No. 9, pp. 910-914.

Zhang, X., et al., "Genotypic effects on tissue culture response of lettuce cotyledons", Journal of Genetics and Breeding. 1992, vol. 46, No. 3, pp. 287-290.

\* cited by examiner

*Primary Examiner* — Ashley K Buran

(74) *Attorney, Agent, or Firm* — Arent Fox LLP

(57) ABSTRACT

The disclosure provides a new and distinct variety of lettuce, NUN 09127 LTL as well as seeds and plants and heads or leaves thereof.

26 Claims, No Drawings ns # LETTUCE VARIETY NUN 09127 LTL

CROSS-REFERENCE TO RELATED APPLICATIONS

The application claims the benefit of U.S. Patent Application Ser. No. 62/549,542, filed Aug. 24, 2017, which is incorporated herein by reference in its entirety.

FIELD OF THE DISCLOSURE

The disclosure relates to the field of plant breeding and, more specifically, to lettuce variety NUN 09127 LTL. The disclosure further relates to vegetative reproductions of NUN 09127 LTL, methods for tissue culture of NUN 09127 LTL and regenerating a plant from such a tissue culture, and to phenotypic variants of NUN 09127 LTL.

BACKGROUND

The goal of plant breeding is to combine various desirable traits in a single variety. Such desirable traits may include greater yield, resistance to diseases, insects or other pests, tolerance to heat and drought, better agronomic quality, higher nutritional value, enhanced growth rate and improved shelf life.

The development of commercial lettuce cultivars or varieties requires the crossing of lettuce plants, and the evaluation of the crosses. Pedigree breeding and recurrent selection are examples of breeding methods are used to develop cultivars from breeding populations. Breeding programs combine desirable traits from two or more varieties or various broad-based sources into breeding pools from which cultivars are developed by selfing and selection of desired phenotypes. The new cultivars are crossed with other varieties and the inbred lines or hybrids from these crosses are evaluated to determine which have commercial potential.

All cultivated forms of lettuce belong to the highly polymorphic species *Lactuca sativa* that is grown for its edible head and leaves. *Lactuca sativa* is in the Asteraceae (Compositae) family. Lettuce is related to chicory, sunflower, aster, dandelion, artichoke and *chrysanthemum*. *L. sativa* is one of about 300 species in the genus *Lactuca*. There are many types of lettuce, and new types are constantly in development. Types of lettuce include Cutting/Leaf, Iceberg/Crisphead, Cos or Romaine, Batavian, Salinas Group, Latin, Butterhead, Great Lakes Group, Eastern (Ithaca) Group, Bibb, Vanguard Group, multileaf or Stem lettuce.

Fresh lettuce is available in the United States year-round although the greatest supply is from May through October. For planting purposes, the lettuce season is typically divided into three categories, early, mid and late, with the coastal areas planting from January to August, and the desert regions planting from August to December. Lettuce is consumed nearly exclusively as fresh, raw product and occasionally as a cooked vegetable.

Lifestyles change and the demand from restaurants and catering firms for colorful and interesting garnish for sandwiches and ready-to-use processed salads continue to rise. As a result, there is a demand for breeding companies to develop new varieties with specific shapes of leaves, specific average size of leaves, glossiness, prominent color and a wide variety of texture, as well as good yield.

SUMMARY OF VARIOUS EMBODIMENTS OF THE DISCLOSURE

The disclosure provides for lettuce variety NUN 09127 LTL, products thereof, and methods of using the same. NUN 09127 LTL is a narrow oakleaf lettuce that can be grown as babyleaf, and is suitable for growing in the open field.

In one aspect, the disclosure provides a seed of lettuce variety NUN 09127 LTL, wherein a representative sample of said seed has been deposited under Accession Number NCIMB 43644. The disclosure also provides for a plurality of seeds of NUN 09127 LTL. The lettuce seed of NUN 09127 LTL may be provided as an essentially homogeneous population of lettuce seed. The population of seed of NUN 09127 LTL may be particularly defined as essentially free from other seed. The seed population may be grown into plants to provide an essentially homogeneous population of lettuce plants as described herein.

The disclosure also provides a plant grown from a seed of lettuce variety NUN 09127 LTL and a plant part thereof. In another aspect, the disclosure provides for an inbred variety of NUN 09127 LTL. The disclosure also provides for a progeny of NUN 09127 LTL. In another aspect, the disclosure provides a plant or a progeny retaining all or all but one, two or three of the "distinguishing characteristics" or all or all but one, two or three of the "morphological and physiological characteristics" of NUN 09127 LTL, and methods for producing that plant or progeny.

In one aspect, the disclosure provides a plant or a progeny having all the physiological and morphological characteristics of variety NUN 09127 LTL when grown under the same environmental conditions. In another aspect, the plant or progeny has all or all but one, two or three of the physiological and morphological characteristics of NUN 09127 LTL when measured under the same environmental conditions and evaluated at significance levels of 1%, 5% or 10% significance (which can also be expressed as a p-value), wherein a representative sample of seed of variety NUN 09127 LTL has been deposited under Accession Number NCIMB 43644. In another aspect, the plant or progeny has all or all but one, two or three of the physiological and morphological characteristics as listed in Table 1 and/or 2 for variety NUN 09127 LTL when measured under the same environmental conditions and evaluated at significance levels of 1%, 5% or 10% significance (which can also be expressed as a p-value).

In another aspect, a plant of NUN 09127 LTL or a progeny thereof has 7, 8, 9, or more or all of the following distinguishing characteristics: 1) average mature leaf width; 2) average mature plant height; 3) average mature plant spread of frame leaves; 4) average mature plant head weight; 5) average mature plant core diameter; 6) typical mature leaf incision depth of margin; 7) typical mature leaf incision density of margin; 8) typical mature leaf indentation of margin; 9) typical mature leaf undulation of apical margin; and 10) typical mature leaf thickness.

In other aspects, the disclosure provides for a plant part obtained from variety NUN 09127 LTL, wherein said plant part is: a leaf, a part of a leaf, a head, a part of a head, a fruit, a part of a fruit, pollen, an ovule, a cell, a petiole, a shoot or a part thereof, a stem or a part thereof, a root or a part thereof, a root tip, a cutting, a seed, a part of a seed, seed coat or another maternal tissue which is part of a seed grown on said variety, hypocotyl, cotyledon, a pistil, an anther, or a flower or a part thereof. Heads and leaves are particularly important plant parts. In another aspect, the plant part obtained from variety NUN 09127 LTL is a cell, optionally a cell in a cell or tissue culture. That cell may be grown into a plant of NUN 09127 LTL.

The disclosure also provides a cell culture of NUN 09127 LTL and a plant regenerated from NUN 09127 LTL, which plant has all the characteristics of NUN 09127 LTL when grown under the same environmental conditions, as well as methods for regenerating NUN 09127 LTL. Alternatively, a regenerated plant may have one characteristic that is different from NUN 09127 LTL.

The disclosure further provides a vegetatively propagated plant of variety NUN 09127 LTL having all or all but one, two or three of the morphological and physiological characteristics of NUN 09127 LTL when grown under the same environmental conditions.

The disclosure furthermore provides a lettuce head and/or a lettuce leaf produced on a plant grown from a seed of NUN 09127 LTL.

In another aspect, the disclosure provides a seed growing or grown on a plant of NUN 09127 LTL (i.e., produced after pollination of the flower of NUN 09127 LTL). Further, an F1 progeny of NUN 09127 LTL is provided.

DEFINITIONS

"Lettuce" refers herein to plants of the species *Lactuca sativa* L. The most commonly eaten parts of a lettuce plant are the head or a leaf. The head comprises a core and leaves, which may be divided in inner and outer leaves.

"Cultivated lettuce" refers to plants of *Lactuca sativa* (e.g., varieties, breeding lines or cultivars of the species *L. sativa* as well as crossbreds thereof, or crossbreds with other *Lactuca sativa* species, or even with other *Lactuca* species), cultivated by humans and having good agronomic characteristics.

"Leaf lettuce" or "cutting lettuce" refers to a type of lettuce with very loose leaves, that does not form a head.

The terms "lettuce plant designated NUN 09127 LTL", "NUN 09127 LTL", "NUN 09127", "inbred NUN 09127", "09127 LTL" or "lettuce 09127" are used interchangeably herein and refer to a lettuce plant of variety NUN 09127 LTL, representative seed of which having been deposited under Accession Number NCIMB 43644.

A "seed of NUN 09127 LTL" refers to a lettuce seed which can be grown into a plant of NUN 09127 LTL, wherein a representative sample of viable seed of NUN 09127 LTL has been deposited under Accession Number NCIMB 43644. A seed can be in any stage of maturity, for example, a mature, viable seed, or an immature, non-viable seed. A seed comprises an embryo and maternal tissues.

An "embryo of NUN 09127 LTL" refers to an embryo as present in a seed of NUN 09127 LTL, a representative sample of said seed of NUN 09127 LTL having been deposited under Accession Number NCIMB 43644.

A "seed grown on NUN 09127 LTL" refers to a seed grown on a mature plant of NUN 09127 LTL or inside a fruit of NUN 09127 LTL. The "seed grown on NUN 09127 LTL" contains tissues and DNA of the maternal parent, NUN 09127 LTL. The "seed grown on NUN 09127 LTL" contains an F1 embryo. When said seed is planted, it grows into a first generation progeny plant of NUN 09127 LTL. Since NUN09127 LTL is an inbred variety and thus highly homozygous, the set of chromosomes inherited by the first generation progeny is predictable.

An "essentially homogeneous population of lettuce seed" is a population of seeds where at least 97%, 98%, 99% or more of the total population of seed are seed of NUN 09127 LTL.

An "essentially homogeneous population of lettuce plants" is a population of plants where at least 97%, 98%, 99% or more of the total population of plants are plants of NUN 09127 LTL.

The phrase "essentially free from other seed" refers to a population of seed where less than 3%, 2%, 1% or less of the total population of seed is seed that is not a lettuce seed or, in another aspect, less than 3%, 2%, 1% or less of the total population of seed is seed that is not seed of NUN 09127 LTL.

"Tissue culture" or "cell culture" refers to a composition comprising isolated cells of the same or a different type or a collection of such cells organized into parts of a plant. Tissue culture of various tissues of lettuce and regeneration of plants is well known and widely published (see, e.g., Teng et al., HortScience. 1992, 27(9): 1030-1032; Teng et al., HortScience. 1993, 28(6): 669-1671; Zhang et al., Journal of Genetics and Breeding. 1992, 46(3): 287-290). Similarly, methods of preparing cell cultures are known in the art.

"USDA descriptors" are the plant variety descriptors described for lettuce in the "Objective description of Variety—Lettuce (*Lactuca sativa* L.)", as published by U.S. Department of Agriculture, Agricultural Marketing Service, Science and Technology, Plant Variety Protection Office, Beltsville, Md. 20705 and which can be downloaded from the world-wide web at ams.usda.gov/under sites/default/files/media/01-Lettuce%20ST-470-01%202015.pdf, and is hereby incorporated by reference in its entirety. "Non-USDA descriptors" are other descriptors suitable for describing lettuce.

"UPOV descriptors" are the plant variety descriptors described for lettuce in the "Guidelines for the Conduct of Tests for Distinctness, Uniformity and Stability," TG/013/11 (Geneva 2006, last updated 2017), as published by UPOV (International Union for the Protection of New Varieties and Plants) and which can be downloaded from the world-wide web at upov.int/under edocs/tgdocs/en/tg013.pdf, and is herein incorporated by reference in its entirety. Likewise, "UPOV methods" to determine specific parameters for the characterization of lettuce are described at upov.int.

"RHS" or "RHS color" refers to the color chart of the Royal Horticultural Society (UK), which publishes a botanical color chart quantitatively identifying colors by a defined numbering system. The chart may be purchased from Royal Horticulture Society Enterprise Ltd. RHS Garden; Wisley, Woking; Surrey GU236QB, UK, e.g., the RHS colour chart 2007.

"Plant part" includes any part of a plant, such as a plant organ (e.g., harvested or non-harvested fruits), a plant cell, a plant protoplast, a plant cell tissue culture or a tissue culture from which a whole plant can be regenerated, a plant cell that is intact in a plant, a clone, a micropropagation, plant callus, a plant cell clump, a plant transplant, a vegetative propagation, a seedling, a fruit, a harvested fruit, a part of a fruit, a leaf, a part of a leaf, pollen, an ovule, an embryo, a petiole, a shoot or a part thereof, a stem or a part thereof, a root or a part thereof, a root tip, a cutting, a seed, a part of a seed, hypocotyl, cotyledon, a scion, a graft, a stock, a rootstock, a pistil, an anther, and a flower or parts of any of these and the like. Seed can be mature or immature. Pollen or ovules may be viable or non-viable. Also, any developmental stage is included, such as seedlings, cuttings prior or after rooting, mature plants or leaves. Alternatively, a plant part may also include a plant seed which comprises one or two sets of chromosomes derived from the parent plant (e.g., from NUN 09127 LTL). An F1 progeny produced from self-pollination of the inbred variety NUN 09127 LTL will thus comprise two sets of chromosomes derived NUN 09127 LTL while an F1 progeny derived from cross-fertilization of NUN 09127 LTL will comprise only one set of chromosomes from NUN 09127 LTL and the other set of chromosomes from the other parent.

"Reference Variety" refers herein to variety Greenflash, a commercial variety from Nunhems B.V., which has been planted in a trial together with NUN 09127 LTL. USDA descriptors of NUN NUN 09127 LTL were compared to the USDA descriptors of Greenflash.

"Head" as used herein refers to lettuce heads, i.e., the plant without the root system, for example substantially all harvested leaves. Encompassed are immature leaves (e.g., "baby leaf") and mature leaves.

The "base" of a plant is the part of a lettuce plant where the leaves are attached to the root system of the plant.

"Core length" of the internal lettuce stem is measured from the base of the cut and trimmed head to the tip of the stem.

"Head weight" refers to the mean weight of saleable lettuce head, cut and trimmed to market specifications. "Head diameter" refers to the mean diameter of the cut and trimmed head, sliced vertically, and measured at the widest point perpendicular to the stem. "Head height" refers to the mean height of the cut and trimmed head, sliced vertically, and measured from the base of the cut stem to the leaf tip. "Core Length to Head Diameter Ratio (CLHD Ratio)" refers to the mean core length/head diameter ratio. It is calculated by dividing the mean core length with the mean head diameter. This is an indication of the head shape and of the ability of a lettuce plant to reduce the amount of surface which is on or close to the ground.

"Harvested plant material" refers herein to plant parts (e.g., leaves or heads detached from the whole plant) which have been collected for further storage and/or further use.

"Yield" means the total weight of all lettuce heads or leaves harvested per hectare of a particular line or variety. It is understood that "yield" expressed as weight of all lettuce heads or leaves harvested per hectare can be obtained by multiplying the number of plants per hectare times the "yield per plant". "Marketable yield" means the total weight of all marketable lettuce heads or leaves harvested per hectare of a particular line or variety, i.e., lettuce heads or leaves suitable for being sold for fresh consumption, having good color, glossiness size and texture and no or very low levels of deficiencies. A "marketable lettuce head or leaf" is a head or leaf that has commercial value.

A plant having "all the physiological and morphological characteristics" of a referred-to-plant means a plant showing the physiological and morphological characteristics of the referred-to-plant when grown under the same environmental conditions, preferably in the same experiment; the referred-to-plant can be a plant from which it was derived, e.g., the progenitor plant, the parent, the recurrent parent, the plant used for tissue- or cell culture, etc. A physiological or morphological characteristic can be a numerical characteristic or a non-numerical characteristic. In one aspect, a plant has "all but one, two or three of the physiological and morphological characteristics" of a referred-to-plant, or "all the physiological and morphological characteristics" of Table 1 and/or 2 or "all or all but one, two or three of the physiological and morphological characteristics" of Table 1 and/or 2.

The physiological and/or morphological characteristics mentioned above are commonly evaluated at significance levels of 1%, 5% or 10% if they are numerical, or for having an identical degree (or type) if not numerical, if measured under the same environmental conditions. For example, a progeny plant or a Single Locus Converted plant or a mutated plant of NUN 09127 LTL may have one or more (or all) of the essential physiological and/or morphological characteristics of said variety listed in Table 1 and/or 2, as determined at the 5% significance level (i.e., p<0.05), when grown under the same environmental conditions.

"Distinguishing characteristics" or "distinguishing morphological and/or physiological characteristics" refers herein to the characteristics which distinguish the new variety from other lettuce varieties, such as the Reference Variety (i.e., are different), when grown under the same environmental conditions. The distinguishing characteristics between NUN 09127 LTL and Reference Variety are described herein and also can be seen in Table 1 and/or Table 2. When comparing NUN 09127 LTL to other varieties, the distinguishing characteristics may be different. In one aspect, the distinguishing characteristics may include one, two, three or more (or all) of the characteristics listed in Table 1 and/or 2. All numerical distinguishing characteristics are statistically significantly different at p<0.05 between NUN 09127 LTL and the other variety (e.g., the Reference Variety).

NUN 09127 LTL has the following distinguishing characteristics when compared to the Reference Variety: 1) average mature leaf width; 2) average mature plant height; 3) average mature plant spread of frame leaves; 4) average mature plant head weight; 5) average mature plant core diameter; 6) typical mature leaf incision depth of margin; 7) typical mature leaf incision density of margin; 8) typical mature leaf indentation of margin; 9) typical mature leaf undulation of apical margin; and 10) typical mature leaf thickness. This can be seen, for example, in Table 1, where the USDA characteristics of NUN 09127 LTL are compared to the characteristics of the Reference Variety, when grown under the same environmental conditions Thus, a lettuce plant "comprising the distinguishing characteristics of NUN 09127 LTL" (such as a progeny plant) refers herein to a plant which does not differ significantly from said variety in the distinguishing characteristics above. Therefore, in one aspect, the disclosure provides a plant that does not differ significantly from NUN 09127 LTL in the distinguishing characteristics above.

Similarity and differences between two different plant lines or varieties can be determined by comparing the number of morphological and/or physiological characteristics that are the same (i.e., statistically not significantly different) or that are different (i.e., statistically significantly different) between the two plant lines or varieties using plants grown under the same environmental conditions. A numerical characteristic is considered to be "the same" when the value for a numeric characteristic is not significantly different at the 1% (p<0.01) or 5% (p<0.05) significance level, using one way analysis of variance (ANOVA), a standard method known to the skilled person. Non-numerical or "degree" or "type" characteristics are considered "the same" when the values have the same "degree" or "type" when scored using USDA and/or UPOV descriptors, if the plants are grown under the same environmental conditions.

"Regeneration" refers to the development of a plant from cell culture or tissue culture or vegetative propagation.

"Vegetative propagation", "vegetative reproduction" or "clonal propagation" are used interchangeably herein and mean a method of taking a plant part and inducing or allowing that plant part to form at least roots, and also refer to the plant or plantlet obtained by that method. Optionally, the vegetative propagation is grown into a mature plant. The skilled person is aware of what plant parts are suitable for use in the method.

"Crossing" refers to the mating of two parent plants. The term encompasses "cross-pollination" and "selfing".

"Selfing" refers to self-pollination of a plant, i.e., the transfer of pollen from the anther to the stigma of the same plant.

"Cross-pollination" refers to the fertilization by the union of two gametes from different plants.

As used herein, the terms "resistance" and "tolerance" are used interchangeably to describe plants that show no symptoms or significantly reduced symptoms to a specified biotic pest, pathogen, abiotic influence or environmental condition compared to a susceptible plant. These terms are optionally also used to describe plants showing some symptoms but that are still able to produce marketable product with an acceptable yield.

The term "traditional breeding techniques" encompasses herein crossing, selfing, selection, doubled haploid production, embryo rescue, protoplast fusion, marker assisted selection, mutation breeding etc. as known to the breeder (i.e., methods other than genetic modification/transformation/transgenic methods), by which, for example, a genetically heritable trait can be transferred from one lettuce line or variety to another. It optionally includes epigenetic modifications.

"Backcrossing" is a traditional breeding technique used to introduce a trait into a plant line or variety. The plant containing the trait is called the donor plant and the plant into which the trait is transferred is called the recurrent parent. An initial cross is made between the donor parent and the recurrent parent to produce a progeny plant. Progeny plants which have the trait are then crossed to the recurrent parent. After several generations of backcrossing and/or selfing the recurrent parent comprises the trait of the donor. The plant generated in this way may be referred to as a "single trait converted plant". The technique can also be used on a parental line of a hybrid.

"Progeny" as used herein refers to a plant obtained from a plant designated NUN 09127 LTL. A progeny may be obtained by regeneration of cell culture or tissue culture or parts of a plant of said variety or selfing of a plant of said variety or by producing seeds of a plant of said variety. In further aspects, progeny may also encompass plants obtained from crossing of at least one plant of said variety with another lettuce plant of the same variety or another variety or line, or with wild lettuce plants. A progeny may comprise a mutation or a transgene. A "first generation progeny" is the progeny directly derived from, obtained from, obtainable from or derivable from the parent plant by, e.g., traditional breeding methods (selfing and/or cross-pollinating) or regeneration (optionally combined with transformation or mutation). Thus, a plant of NUN 09127 LTL is the male parent, the female parent or both of a first-generation progeny of NUN 09127 LTL. Progeny may have all the physiological and morphological characteristics of NUN 09127 LTL when grown under the same environmental conditions. Using methods such as backcrossing, recurrent selection, mutation or transformation, one or more specific characteristics may be introduced into said variety, to provide or a plant comprising all but 1, 2, or 3 of the morphological and physiological characteristics of NUN 09127 LTL.

The terms "gene converted" or "conversion plant" or "single locus converted plant" in this context refer to lettuce plants which are developed by backcrossing wherein essentially all of the desired morphological and physiological characteristics of the parent variety or line are recovered, in addition to the one or more genes transferred into the parent via the backcrossing technique (optionally including reverse breeding or reverse synthesis of breeding lines) or via genetic engineering or through mutation breeding. Likewise, a "Single Locus Converted (Conversion) Plant" refers to plants developed by plant breeding techniques comprising or consisting of mutation and/or by genetic transformation and/or by backcrossing, wherein essentially all of the desired morphological and physiological characteristics of a lettuce variety are recovered in addition to the characteristics of the single locus having been transferred into the variety via the backcrossing technique. In case of a hybrid, the gene may be introduced in the male or female parental line.

"Marker" refers to a readily detectable phenotype, preferably inherited in codominant fashion (both alleles at a locus in a diploid heterozygote are readily detectable), with no environmental variance component, i.e., a heritability of 1.

"Average" refers herein to the arithmetic mean.

The term "mean" refers to the arithmetic mean of several measurements. The skilled person understands that the appearance of a plant depends to some extent on the growing conditions of said plant. Thus, the skilled person will know suitable growing conditions for NUN 09127 LTL. The mean, if not indicated otherwise within this application, refers to the arithmetic mean of measurements on at least 10 different, randomly selected plants of a variety or line.

DETAILED DESCRIPTION OF VARIOUS EMBODIMENTS OF THE DISCLOSURE

The disclosure relates to a plant of NUN 09127 LTL, wherein a representative sample of seeds of said variety was deposited under the Budapest Treaty, with Accession number NCIMB 43644. NUN 09127 LTL is a narrow oakleaf lettuce that can be grown as babyleaf, and is suitable for growing in the open field.

The disclosure also relates to a seed of lettuce variety, referred to as NUN 09127 LTL, wherein a representative sample of said seed was deposited under the Budapest Treaty, with Accession number NCIMB 43644.

In another aspect, the disclosure provides for a lettuce plant part of variety NUN 09127 LTL, preferably a leaf or head, a representative sample of seed from said variety has been deposited under the Budapest Treaty, with Accession number NCIMB 43644.

A seed of inbred variety NUN 09127 LTL is obtainable by selfing the variety and harvesting the seeds produced. The resultant seeds can be grown to produce plants of said variety. In one aspect, a seed or a plurality of seeds of said variety are packaged into a container of any size or type (e.g., bags, cartons, cans, etc.). The seed may be disinfected, primed and/or treated with various compounds, such as seed coatings or crop protection compounds. The seed produces a plant of NUN 09127 LTL.

Also provided is a plant of NUN 09127 LTL, or a head or leaf or other plant part thereof, produced from a seed, wherein a representative sample of said seeds has been deposited under the Budapest Treaty, with Accession Number NCIMB 43644.

Also provided is a plant part obtained from variety NUN 09127 LTL, wherein said plant part is a leaf, a part of a leaf, a head, a part of a head, a fruit, a part of a fruit, pollen, an ovule, a cell, a petiole, a shoot or a part thereof, a stem or a part thereof, a root or a part thereof, a root tip, a cutting, a seed, a part of a seed, seedcoat or another maternal tissue which is part of a seed grown on said variety, hypocotyl, cotyledon a pistil, an anther, or a flower or a part thereof.

Heads and leaves are particularly important plant parts. In a further aspect, the plant part obtained from variety NUN 09127 LTL is a cell, optionally a cell in a cell or tissue culture. The cell may be grown into a plant of NUN 09127 LTL. A part of NUN 09127 LTL (or of a progeny of that variety or of a plant having all physiological and/or morphological characteristics but one, two or three of NUN 09127 LTL) further encompasses any cells, tissues, organs obtainable from the seedlings or plants in any stage of maturity.

The disclosure also provides for a food or feed product or a processed product comprising or consisting of a plant part described herein. Preferably, the plant part is a lettuce head or leaf or part thereof and/or an extract from a leaf or another plant part described herein comprising at least one cell of NUN 09127 LTL. The food or feed product may be fresh or processed, e.g., dried, grinded, powdered, pickled, chopped, cooked, roasted, in a sauce, in a sandwich, pasted, puréed or concentrated, juiced, pickled, canned, steamed, boiled, fried, blanched and/or frozen, etc.

Such a plant part of NUN 09127 LTL can be stored and/or processed further. The disclosure thus also provides for a food or feed product comprising one or more of such parts, such as canned, chopped, cooked, roasted, in a sauce, in a sandwich, pasted, puréed or concentrated, juiced, frozen, dried, pickled, or powdered lettuce heads or leaves from NUN 09127 LTL or from progeny of said variety, or from a derived variety, such as a plant having all but one, two or three physiological and/or morphological characteristics of NUN 09127 LTL.

In another aspect, the disclosure provides for a lettuce head or leaf of variety NUN 09127 LTL, or a part of a head or leaf of said variety. The head or leaf can be in any stage of maturity, for example, immature or mature. In another embodiment, the disclosure provides for a container comprising or consisting of a plurality of harvested lettuce heads or leaves or parts of lettuce heads or leaves of said variety, or fruits of progeny thereof, or heads or leaves of a derived variety. Marketable lettuce heads or leaves are generally sorted by size and quality after harvest. Alternatively, the lettuce heads or leaves can be sorted by leaf size, shape, texture, glossiness or color.

In another aspect, the plant, plant part or seed of NUN 09127 LTL is inside one or more containers. For example, the disclosure provides containers, such as cans, boxes, crates, bags, cartons, Modified Atmosphere Packaging, films (e.g. biodegradable films), etc. comprising a plant or a plant part or a seed (fresh and/or processed) of NUN 09127 LTL. In a particular aspect, the container comprises a plurality of seeds of NUN 09127 LTL, or a plurality of plant parts of NUN 09127 LTL.

The disclosure further relates to a lettuce variety, referred to as NUN 09127 LTL, which—when compared to its Reference Variety Greenflash—has the following distinguishing characteristics: 1) average mature leaf width; 2) average mature plant height; 3) average mature plant spread of frame leaves; 4) average mature plant head weight; 5) average mature plant core diameter; 6) typical mature leaf incision depth of margin; 7) typical mature leaf incision density of margin; 8) typical mature leaf indentation of margin; 9) typical mature leaf undulation of apical margin; and 10) typical mature leaf thickness, where the characteristics are determined at the 5% significance level for plants grown under the same environmental conditions. Also encompassed are parts of that plant.

In one aspect, a plant of NUN 09127 LTL or a progeny plant thereof, comprises all of the following morphological and/or physiological characteristics (i.e., average values of distinguishing characteristics, as indicated on the USDA Objective description of variety—lettuce (unless indicated otherwise)): 1) average mature leaf width; 2) average mature plant height; 3) average mature plant spread of frame leaves; 4) average mature plant head weight; 5) average mature plant core diameter; 6) typical mature leaf incision depth of margin; 7) typical mature leaf incision density of margin; 8) typical mature leaf indentation of margin; 9) typical mature leaf undulation of apical margin; and 10) typical mature leaf thickness, where the characteristics are determined at the 5% significance level for plants grown under the same environmental conditions. An example of values for the distinguishing characteristics collected in a trial run according to UDSA requirements can be found in Table 1. A part of this plant is also provided.

NUN 09127 LTL may further exhibit one or more of the following characteristics as described in Table 1 and/or 2 for NUN 09127 LTL: a) leaf length/width ratio, b) mature leaf color (green, RHS 137B), c) mature leaf blistering, and/or d) ratio of frame leaf diameter/core diameter.

In another aspect, NUN 09094 LTL has resistance to Downy mildew (*Bremia lactucae*) isolate Bl: 1-33 that is 9 (present) and to Lettuce Mosaic Virus (LMV) Strain Ls 1 that is 9 (present) according to UPOV standards. See UPOV TG/13/11.

The disclosure further provides a lettuce plant which does not differ from the physiological and morphological characteristics of the plant of NUN 09127 LTL as determined at the 1%, 2%, 3%, 4% or 5% significance level when grown under the same environmental conditions. In a particular aspect, the plants are measured in the same trial (e.g., the trial is conducted as recommended by the USDA or UPOV). The disclosure also comprises a part of said plant, preferably a head or a leaf.

The disclosure also provides a tissue or cell culture comprising cells of NUN 09127 LTL. Such a tissue culture can, for example, be grown on plates or in liquid culture, or be frozen for long term storage. The cells of NUN 09127 LTL used to start the culture can be selected from any plant part suitable for vegetative reproduction, or in a particular aspect, can be cells of an embryo, meristem, a cotyledon, a hypocotyl, pollen, a leaf, an anther, a root, a root tip, a pistil, a petiole, a flower, a fruit, seed or a stem. In another particular aspect, the tissue culture does not contain somaclonal variation or has reduced somaclonal variation. The skilled person is familiar with methods to reduce or prevent somaclonal variation, including regular re-initiation.

In one aspect, the disclosure provides a lettuce plant regenerated from the tissue or cell culture of NUN 09127 LTL, wherein the regenerated plant is not significantly different from NUN 09127 LTL in all, or all but one, two or three, of the physiological and morphological characteristics (determined at the 5% significance level when grown under the same environmental conditions). Optionally, the plant has one, two or three the physiological and morphological characteristics that are affected by a mutation or by transformation. In another aspect, the disclosure provides a lettuce plant regenerated from the tissue or cell culture of NUN 09127 LTL, wherein the plant has all of the physiological and morphological characteristics of said variety determined at the 5% significance level when grown under the same environmental conditions. Similarity or difference of a characteristic is determined by measuring that characteristics on a representative number of plants grown under the same environmental conditions, determining whether type/degree characteristics are the same and determining whether numerical characteristics are different at the 5% significance level.

NUN 09127 LTL, or its progeny, or a plant having all physiological and/or morphological characteristics but one, two or three which are different from those of NUN 09127 LTL, can also be reproduced using vegetative reproduction methods. Therefore, the disclosure provides for a method of producing a plant, or a plant part, of NUN 09127 LTL, comprising vegetative propagation of said variety. Vegetative propagation comprises regenerating a whole plant from a plant part of NUN 09127 LTL or from a progeny or from or a plant having all physiological and/or morphological characteristics of said variety but one, two or three different characteristics, such as a cutting, a cell culture or a tissue culture.

The disclosure also provides methods of vegetatively propagating a part of the plant of the disclosure NUN 09127 LTL. In certain aspects, the method comprises: (a) cultivating tissue or cells capable of being propagated from NUN 09127 LTL to obtain proliferated shoots; and (b) rooting said proliferated shoots, to obtain rooted plantlets. Steps (a) and (b) may also be reversed, i.e., first cultivating said tissue to obtain roots and then cultivating the tissue to obtain shoots, thereby obtaining rooted plantlets. The rooted plantlets may then be further grown, to obtain plants. In one embodiment, the method further comprises step (c) growing plants from said rooted plantlets. Therefore, the method also comprises regenerating a whole plant from a part of NUN 09127 LTL. In a particular aspect, the part of the plant to be propagated is is a cutting, a cell culture or a tissue culture.

The disclosure also provides for a vegetatively propagated plant of variety NUN 09127 LTL (or from progeny of NUN 09127 LTL or from or a plant having all but one, two or three physiological and/or morphological characteristics of NUN 09127 LTL), wherein the plant has all of the morphological and physiological characteristics of NUN 09127 LTL when the characteristics are determined at the 5% significance level for plants grown under the same conditions. In another aspect, the propagated plant has all but one, two or three of the morphological and physiological characteristics of NUN 09127 LTL when the characteristics are determined at the 5% significance level for plants grown under the same conditions. A part of said propagated plant or said propagated plant with one, two or three differences is also included.

In another aspect, the disclosure provides a method for producing a plant part, preferably a head or leaf, comprising growing a plant of NUN 09127 LTL until it develops at least one leaf or develops a head, and collecting the fruit. Preferably, the head or leaf is collected at harvest maturity. In another aspect, the leaf is collected at babyleaf stage. A plant of NUN 09127 LTL can be produced by seeding directly in the soil (e.g., field) or by germinating the seeds in controlled environment conditions (e.g., greenhouses) and then transplanting the seedlings into the field (see, e.g., Gonai et al., J. of Exp. Bot., 55(394): 111, 2004; http://anrcatalog.ucanr.edu/pdf/7215.pdf; http://anrcatalog.ucanr.edu/pdf/7216.pdf). Lettuce may also be grown in tunnels. Moreover, said variety can be grown in hydroponic cultures as described in, e.g., US2008/0222949, which is herein incorporated by reference in its entirety, and the skilled person is familiar with various types of hydroponic cultures. Alternatively, seed of NUN 09127 LTL may be grown on peat block for use as root ball lettuce. Furthermore, NUN 09127 LTL may be combined with 1, 2 or 3 other lettuce varieties to be grown as "composite lettuce" (see, e.g., EP1197137, which is herein incorporated by reference in its entirety).

In still another aspect, the disclosure provides a method of producing a lettuce plant, comprising crossing a plant of NUN 09127 LTL with a second lettuce plant at least once, allowing seed to develop and optionally harvesting said progeny seed. The skilled person can select progeny from said crossing. Optionally, the progeny (grown from the progeny seed) is crossed twice, thrice, or four, five, six or seven times, and allowed to set seed. In one aspect, the first "crossing" further comprises planting seeds of a first and a second parent lettuce plant, often in proximity so that pollination will occur; for example, mediated by insect vectors. Alternatively, pollen can be transferred manually. Where the plant is self-pollinated, pollination may occur without the need for direct human intervention other than plant cultivation. After pollination, the plant can produce seed.

The disclosure also provides a method for developing a plant in a breeding program, using NUN 09127 LTL, or its parts as a source of plant breeding material. Suitable plant breeding techniques are recurrent selection, backcrossing, pedigree breeding, mass selection, mutation breeding and/or genetic marker enhanced selection. In one aspect, the method comprises crossing NUN 09127 LTL or its progeny, or a plant comprising all but 1, 2, or 3 or more of the morphological and physiological characteristics of NUN 09127 LTL (e.g., as listed in Table 1 and/or 2), with a different plant, and wherein one or more offspring of the crossing are subject to one or more plant breeding techniques: recurrent selection, backcrossing, pedigree breeding, mass selection, mutation breeding and genetic marker enhanced selection (see e.g., Vidaysky and Czosnek, (1998) Phytopathology 88(9): 910-4). For breeding methods in general see Principles of Plant Genetics and Breeding, 2007, George Acquaah, Blackwell Publishing, ISBN-13: 978-1-4051-3646-4.

In yet another aspect, the disclosure provides a method of producing a plant, comprising selfing a plant of variety NUN 09127 LTL one or more times, and selecting a progeny plant from said selfing. In one aspect, the progeny plant retains all or all but one, two or three of the physiological and morphological characteristic of NUN 09127 LTL described above when grown under the same environmental conditions. In a different aspect, the progeny plant comprises all of the physiological and morphological characteristic of NUN 09127 LTL of Table 1 and Table 2.

In other aspects, the disclosure provides a progeny plant of variety NUN 09127 LTL such as a progeny plant obtained by further breeding of NUN 09127 LTL. Further breeding with NUN 09127 LTL includes selfing that variety and/or cross-pollinating NUN 09127 LTL with another lettuce plant one or more times. In particular, the disclosure provides for a progeny plant that retains all the morphological and physiological characteristics of NUN 09127 LTL or, in another aspect, a progeny plant that retains all, or all but one, two or three, of the morphological and physiological characteristics of NUN 09127 LTL, optionally all or all but one, two or three of the characteristics as listed in Table 1 and/or 2, determined at the 5% significance level for numerical characteristics, when grown under the same environmental conditions. In another aspect, the progeny is a first-generation progeny, e.g., the ovule or the pollen (or both) used in the crossing is an ovule or pollen of NUN 09127 LTL, where the pollen comes from an anther of NUN 09127 LTL and the ovule comes from an ovary of NUN 09127 LTL. In another aspect, the disclosure provides for a vegetative reproduction of the variety and a plant having all, or all but 1, 2, or 3 of the physiological and morphological characteristics of NUN 09127 LTL (e.g., as listed in Table 1 and/or 2).

The disclosure also provides a method for collecting pollen of NUN 09127 LTL, comprising collecting pollen from a plant of NUN 09127 LTL. Alternatively, the method comprises growing a plant of NUN 09127 LTL until at least one flower contains pollen and collecting the pollen. In a particular aspect, the pollen is collected when it is mature or ripe. A suitable method for collecting pollen comprises collecting anthers or the part of the anther that contains pollen, for example, by cutting the anther or the part of the anther off. Pollen can be collected in a container. Optionally, collected pollen can be used to pollinate a lettuce flower.

The morphological and/or physiological differences between two different individual plants described herein (e.g., between NUN 09127 LTL and a progeny of NUN 09127 LTL) or between a plant of NUN 09127 LTL or progeny of said variety, or a plant having all, or all but 1, 2, or 3, of the physiological and morphological characteristics of NUN 09127 LTL (or all, or all but 1, 2, or 3 of the characteristics as listed in Table 1 and/or 2) and another known variety can easily be established by growing said variety next to each other or next to the other variety (in the same field, under the same environmental conditions), preferably in several locations which are suitable for said lettuce cultivation, and measuring morphological and/or physiological characteristics of a number of plants (e.g., to calculate an average value and to determine the variation range/uniformity within the variety). For example, trials can be carried out in Acampo Calif., USA (N 38 degrees 07'261"/W 121 degrees 18' 807", USA, whereby various characteristics, for example, maturity, leaf shape, size and texture, leaf color and glossiness, bolt shape, surface and length, flower size and color, head weight, disease resistance, insect resistance and resistance to physiological stress, can be measured and directly compared for species of lettuce. Thus, the disclosure comprises lettuce plant having one, two or three physiological and/or morphological characteristics which are different from those of the plant of NUN 09127 LTL and which otherwise has all the physiological and morphological characteristics of the plant of NUN 09127 LTL, when determined at the 5% significance level for plants grown under the same environmental conditions. In another aspect, the different characteristic is affected by a mutation, optionally induced mutation, or by transformation.

The morphological and physiological characteristics (and the distinguishing characteristics) of NUN 09127 LTL are provided, for example, in Table 1 and/or 2. Encompassed herein is also a plant obtainable from NUN 09127 LTL (e.g., by selfing and/or crossing and/or backcrossing with said variety and/or progeny of said variety) comprising all or all but one, two or three of the physiological and morphological characteristics of NUN 09127 LTL listed in Table 1 and/or 2 as determined at the 5% significance level for numerical characteristics or identical for non-numerical characteristics when grown under the same environmental conditions and/or comprising one or more (or all; or all except one, two or three) characteristics when grown under the same environmental conditions. The morphological and/or physiological characteristics may vary somewhat with variation in the environment (such as temperature, light intensity, day length, humidity, soil, fertilizer use), which is why a comparison under the same environmental conditions is preferred. Colors can best be measured using the Royal Horticultural Society (RHS) Chart.

In yet a further aspect, the disclosure provides for a method of producing a new lettuce plant. The method comprises crossing NUN 09127 LTL, or a plant comprising all but 1, 2, or 3 of the morphological and physiological characteristics of NUN 09127 LTL (as listed in Table 1 and/or 2), or a progeny thereof, either as male or as female parent, with a second lettuce plant (or a wild relative of lettuce) one or more times, and/or selfing a lettuce plant of NUN 09127 LTL, or a progeny plant thereof, one or more times, and selecting progeny from said crossing and/or selfing. The second lettuce plant may for example be a line or variety of the species *Lactuca sativa* or even other *Lactuca* species.).

The disclosure provides for methods of producing plants which retain all the morphological and physiological characteristics of a plant described herein. The disclosure also provides for methods of producing a plant comprising all but 1, 2, or 3 or more of the morphological and physiological characteristics of NUN 09127 LTL (e.g., as listed in Table 1 and/or 2), but which are still genetically closely related to said variety. The relatedness can, for example be determined by fingerprinting techniques (e.g., making use of isozyme markers and/or molecular markers such as Single-nucleotide polymorphism (SNP) markers, amplified fragment length polymorphism (AFLP) markers, microsatellites, minisatellites, Random Amplified Polymorphic DNA (RAPD) markers, restriction fragment length polymorphism (RFLP) markers and others). A plant is "closely related" to NUN 09127 LTL if its DNA fingerprint is at least 80%, 90%, 95% or 98% identical to the fingerprint of NUN 09127 LTL. In a particular aspect, AFLP markers are used for DNA fingerprinting (Vos et al. 1995, Nucleic Acid Research 23: 4407-4414). A closely related plant may have a Jaccard's Similarity index of at least about 0.8, preferably at least about 0.9, 0.95, 0.98 or more (Parvathaneni et al., J. Crop Sci. Biotech. 2011 (March) 14 (1): 39-43).

The disclosure also provides a plant and a variety obtained or selected by applying these methods on NUN 09127 LTL. Such a plant may be produced by crossing and/or selfing, or alternatively, a plant may simply be identified and selected amongst plants of said variety, or progeny of said variety, e.g. by identifying a variant within NUN 09127 LTL or within progeny of said variety (e.g. produced by selfing) which variant differs from NUN 09127 LTL in one, two or three of the morphological and/or physiological characteristics (e.g., in one, two or three distinguishing characteristics), e.g. those listed in Table 1 and/or 2 or others. In one aspect, the disclosure provides a lettuce plant having a Jaccard's Similarity index with NUN 09127 LTL of at least 0.8, e.g. at least 0.85, 0.9, 0.95, 0.98 or even at least 0.99.

In some aspects, the disclosure provides a lettuce plant comprising genomic DNA having at least 95%, 96%, 97%, 98% or 99% sequence identity compared to the genomic DNA sequence of a plant of NUN 09127 LTL as deposited under Accession Number NCIMB 43644. In some aspects, the lettuce plant further comprises all or all but 1, 2, or 3 of the morphological and physiological characteristics of NUN 09127 LTL (e.g., as listed in Table 1 and/or 2). In other aspects, the lettuce plant is a hybrid or other derived from a seed or plant of NUN 09127 LTL. In other aspects, the lettuce plant comprises the distinguishing characteristics of NUN 09127 LTL.

For the purpose of this disclosure, the "sequence identity" of nucleotide sequences, expressed as a percentage, refers to the number of positions in the two optimally aligned sequences which have identical residues (×100) divided by the number of positions compared. A gap, i.e., a position in the pairwise alignment where a residue is present in one sequence but not in the other, is regarded as a position with non-identical residues. A pairwise global sequence alignment of two nucleotide sequences is found by aligning the two sequences over the entire length according to the Needleman and Wunsch global alignment algorithm described in Needleman and Wunsch, 1970, J. Mol. Biol. 48(3):443-53). A full implementation of the Needleman-Wunsch global alignment algorithm is found in the needle program in The European Molecular Biology Open Software Suite (EMBOSS, Rice et al., Trends in Genetics June 2000, vol. 16, No. 6. pp. 276-277).

The disclosure also provides methods for determining the identity of parental lines of plants described herein, in particular the identity of the female line. US 2015/0126380, which is hereby incorporated by reference, relates to a non-destructive method for analyzing maternal DNA of a seed. In this method, the DNA is dislodged from the seed coat surface and can be used to collect information on the genome of the maternal parent of the seed. This method for analyzing maternal DNA of a seed comprises contacting a seed with a fluid to dislodge DNA from the seed coat surface, and analyzing the DNA thus dislodged from the seed coat surface using methods known in the art. The skilled person is thus able to determine whether a seed has grown on a plant of a plant of NUN 09127 LTL or is a progeny of said variety, because the seed coat of the seed is a maternal tissue genetically identical to NUN 09127 LTL. Since NUN 09127 LTL is an inbred variety, with a very high degree of homozygosity, any F1 progeny will inherit the same, predictable, set of chromosomes from its parent. Thus, the skilled person will also be able to identify maternal tissues of a seed grown on a F1 progeny of NUN 09127 LTL, using the methods described in US 2015/0126380. In another particular aspect, the skilled person can determine the identity of the female parental line of NUN 09127 LTL by analyzing the seed coat of a seed of that variety. In another aspect, the skilled person can determine whether a seed is grown on NUN 09127 LTL.

By crossing and/or selfing (one or more) single traits may be introduced into NUN 09127 LTL (e.g., using backcrossing breeding schemes), while retaining the remaining morphological and/or physiological characteristics of said variety and/or while retaining one or more or all distinguishing characteristics. A single trait converted plant may thereby be produced. For example, disease resistance genes may be introduced, genes responsible for one or more quality traits, yield, etc. Both single genes (e.g., dominant or recessive) and one or more QTLs (quantitative trait loci) may be transferred into NUN 09127 LTL by breeding with said variety.

Any pest or disease resistance genes may be introduced into NUN 09127 LTL, progeny of NUN 09127 LTL or into a plant comprising all but 1, 2, or 3 or more of the morphological and physiological characteristics of NUN 09127 LTL (e.g., as listed in Table 1). Resistance to one or more of the following diseases or pests may be introduced into plants described herein: Downy mildew, Powdery mildew, *Sclerotinia* rot, *Sclerotinia* drop, *Botrytis* (Grey Mold), *Verticillium* Wilt, *Pseudomonas* spp. (Bacterial Soft Rot), Bacterial Leaf Spot, Anthracnose, Bottom rot, Corky root rot, Lettuce mosaic virus, Turnip mosaic virus, Tomato bushy stunt virus (Dieback), Big vein, Cabbage Loopers, Root Aphid, Green Peach Aphid, Lettuce aphid, Pea leafminer, Beet western yellows and aster yellows. Other resistance genes, against pathogenic viruses (e.g. Lettuce infectious yellows virus (LIYV), lettuce mosaic virus (LMV), Cucumber mosaic virus (CMV), Beet western yellows virus (BWYV), Alfalfa mosaic virus (AMV)), fungi, bacteria, nematodes, insects or other pests may also be introduced. In one aspect, resistance against *Nasonovia ribisnigri* biotype Nr:0 and/or Nr:1 is introduced in a plant disclosed herein. Also, any resistances to physiological stresses may be introduced into a plant described herein, or progeny thereof or into a plant comprising all but 1, 2, or 3 or more of the morphological and physiological characteristics of said plant (e.g., as listed in Table 1 and/or 2). Resistance against one or more of the following may be introduced into plants described herein: Tipburn, Heat, Drought, Cold, Salt and/or Brown rob (Rib discoloration/rib blight).

The disclosure also provides a method for developing a lettuce plant in a lettuce breeding program, using a lettuce plant described herein, or its parts as a source of plant breeding material. Suitable plant breeding techniques are recurrent selection, backcrossing, pedigree breeding, mass selection, mutation breeding and/or genetic marker enhanced selection. In one aspect, the method comprises crossing NUN 09127 LTL or progeny of said variety, or a plant comprising all but 1, 2, or 3 or more of the morphological and physiological characteristics of NUN 09127 LTL (e.g., as listed in Table 1 and/or 2), with a different lettuce plant, and wherein one or more offspring of the crossing are subject to one or more plant breeding techniques: recurrent selection, backcrossing, pedigree breeding, mass selection, mutation breeding and genetic marker enhanced selection (see e.g., Martin et al. 2008, Australian Journal of Crop Science 1(2): 43-46). For breeding methods in general, see Principles of Plant Genetics and Breeding, 2007, George Acquaah, Blackwell Publishing, ISBN-13: 978-1-4051-3646-4.

The disclosure also provides a lettuce plant comprising at least a first set of the chromosomes of lettuce variety NUN 09127 LTL, a sample of seed of said variety having been deposited under Accession Number NCIMB 43644; optionally further comprising a single locus conversion or a mutation, wherein said plant has essentially all of the morphological and physiological characteristics of the plant comprising at least a first set of the chromosomes of said variety. In another embodiment, this single locus conversion or mutation confers a trait, wherein the trait is yield, nutritional value, taste, color, crunchiness, male sterility, herbicide tolerance, insect resistance, pest resistance, disease resistance, environmental stress tolerance, modified carbohydrate metabolism and/or modified protein metabolism.

In one embodiment, a plant of NUN 09127 LTL may also be mutated (by e.g., irradiation, chemical mutagenesis, heat treatment, etc.) and mutated seeds or plants may be selected in order to change one or more characteristics of said variety. Methods such as TILLING may be applied to lettuce populations in order to identify mutants. Similarly, NUN 09127 LTL may be transformed and regenerated, whereby one or more chimeric genes are introduced into the variety or into a plant comprising all but 1, 2, 3, or more of the morphological and physiological characteristics (e.g., as listed in Table 1 and/or 2). Transformation can be carried out using standard methods, such as *Agrobacterium tumefaciens* mediated transformation or biolistics, followed by selection of the transformed cells and regeneration into plants. A desired trait (e.g., gene(s) conferring pest or disease resistance, herbicide, fungicide or insecticide tolerance, etc.) can be introduced into NUN 09127 LTL, or progeny of said variety, by transforming said variety or progeny of said variety with a transgene that confers the desired trait, wherein the transformed plant retains all or all but one, two or three of the phenotypic and/or morphological and/or physiological characteristics of NUN 09127 LTL or the progeny of said variety and contains the desired trait.

The disclosure also provides a plant or a cell of a plant comprising a desired trait produced by mutating a plant of variety NUN 09127 LTL or a cell thereof and selecting a plant the desired trait, wherein the mutated plant retains all or all but one of the phenotypic and morphological characteristics of said variety, optionally as described for each variety in in Table 1 and/or 2, and contains the desired trait and wherein a representative sample of seed of variety NUN 09127 LTL has been deposited under Accession Number NCIMB 43644. In a further embodiment, the desired trait is yield, nutritional value, taste, color, crunchiness, male sterility, herbicide tolerance, insect resistance, pest resistance, disease resistance, environmental stress tolerance, modified carbohydrate metabolism and/or modified protein metabolism.

In one aspect, the disclosure provides a method for inducing mutation in NUN 09127 LTL comprising:
 a. exposing a seed, a plant or a plant part or a cell of NUN 09127 LTL to a mutagenic compound or to radiation, wherein a representative sample of seed of NUN 09127 LTL is deposited under Accession Number NCIMB 43644;
 b. selecting a seed, a plant or a plant part or a cell of NUN 09127 LTL having a mutation; and
 c. optionally growing and/or multiplying the seed, plant or plant part or cell of NUN 09127 LTL having the mutation.

The disclosure also provides a plant having one, two or three physiological and/or morphological characteristics which are different from those of NUN 09127 LTL, and which otherwise has all the physiological and morphological characteristics of said variety, wherein a representative sample of seed of variety NUN 09127 LTL has been deposited under Accession Number NCIMB 43644. In particular, variants which differ from NUN 09127 LTL in none, one, two or three of the characteristics mentioned in Table 1 and/or 2 are encompassed.

A part of NUN 09127 LTL (or of progeny of said variety or of a plant having all physiological and/or morphological characteristics but one, two or three which are different from those of said variety) encompasses any cells, tissues, organs obtainable from the seedlings or plants, such as but not limited to: a lettuce leaf or a part thereof, a lettuce head, a cutting, hypocotyl, cotyledon, seed coat, pollen and the like. Such parts can be stored and/or processed further. The disclosure further provides for food or feed products comprising a part of NUN 09127 LTL or a part of progeny of said variety, or a part of a plant having all but one, two or three physiological and/or morphological characteristics of NUN 09127 LTL, comprising one or more of such parts, optionally processed (such as canned, chopped, cooked, roasted, in a sauce, in a sandwich, pasted, puréed or concentrated, juiced, frozen, dried, pickled, or powdered).

In one aspect, the disclosure provides for a haploid plant and/or a doubled haploid plant of NUN 09127 LTL, or of a plant having all but one, two or three physiological and/or morphological characteristics of NUN 09127 LTL, or progeny of any of these, is encompassed herein. Haploid and doubled haploid (DH) plants can, for example, be produced by cell or tissue culture and chromosome doubling agents and regeneration into a whole plant. DH production chromosome doubling may be induced using known methods, such as colchicine treatment or the like. In one aspect, the method comprises inducing a cell or tissue culture with a chromosome doubling agent, and regenerating the cells or tissues into a whole plant.

In another aspect, the disclosure comprises a method for making doubled haploid cells from haploid cells of NUN 09127 LTL is comprising doubling cells of NUN NUN 09127 LTL with a doubling agent, such as colchicine treatment (Nikolova and Niemirowicz-Szczytt (1996) Acta Soc Bot Pol 65:311-317).

In any of the above methods where the single locus conversion concerns a trait, the trait may be yield or pest resistance or disease resistance. In one aspect, the trait is disease resistance and the resistance is conferred to Downy mildew, Powdery mildew, *Sclerotinia* rot, *Sclerotinia* drop, *Botrytis* (Grey Mold), *Verticillium* Wilt, *Pseudomonas* spp. (Bacterial Soft Rot), Bacterial Leaf Spot, Anthracnose, Bottom rot, Corky root rot, Lettuce mosaic virus, Turnip mosaic virus, Tomato bushy stunt virus (Dieback), Big vein, Cabbage Loopers, Root Aphid, Green Peach Aphid, Lettuce aphid, Pea leafminer, Beet western yellows and aster yellows, pathogenic viruses (e.g. Lettuce infectious yellows virus (LIYV), lettuce mosaic virus (LMV), Cucumber mosaic virus (CMV), Beet western yellows virus (BWYV), Alfalfa mosaic virus (AMV)), fungi, bacteria, nematodes or insects. In one aspect, resistance against *Nasonovia ribisnigri* biotype Nr:0 and/or Nr:1 is introduced in a plant disclosed herein. Also, any resistances to physiological stresses may be introduced into a plant described herein, or progeny thereof or into a plant comprising all but 1, 2, or 3 or more of the morphological and physiological characteristics of said plant (e.g., as listed in Table 1 and/or 2). Resistance against one or more of the following may also be introduced into plants of the disclosure: Tipburn, Heat, Drought, Cold, Salt and/or Brown rob (Rib discoloration/rib blight).

Also provided is a plant part obtainable from variety NUN 09127 LTL or from progeny of said variety or from a plant having all but one, two or three physiological and/or morphological characteristics which are different from those of NUN 09127 LTL, or from a vegetatively propagated plant of NUN 09127 LTL (or from its progeny or from a plant having all or all but one, two or three physiological and/or morphological characteristics which are different from those of NUN 09127 LTL), wherein the plant part is a leaf, a harvested leaf, a part of a leaf, a head, a harvested head, a part of a head, a fruit, a harvested fruit, a part of a fruit, pollen, an ovule, a cell, a petiole, a shoot or a part thereof, a stem or a part thereof, a root or a part thereof, a root tip, a cutting, a seed, a part of a seed, seed-coat or another maternal tissue which is part of a seed grown on NUN 09127 LTL, or hypocotyl, cotyledon, a pistil, an anther, and a flower or a part thereof.

In another aspect, the disclosure provides a method of determining the genotype of a plant described herein comprising detecting in the genome (e.g., a sample of nucleic acids) of the plant at least a first polymorphism or an allele. The skilled person is familiar with many suitable methods of genotyping, detecting a polymorphism or detecting an allele including restriction fragment length polymorphism identification (RFLP) of genomic DNA, random amplified polymorphic detection (RAPD) of genomic DNA, amplified fragment length polymorphism detection (AFLP), polymerase chain reaction (PCR), DNA sequencing, allele specific oligonucleotide (ASO) probes, and hybridization to DNA microarrays or beads. Alternatively, the entire genome could be sequenced. The method may, in certain embodiments, comprise detecting a plurality of polymorphisms in the genome of the plant, for example, by obtaining a sample of nucleic acid from a plant and detecting in said nucleic acids a plurality of polymorphisms. The method may further comprise storing the results of the step of detecting the plurality of polymorphisms on a computer readable medium.

The disclosure also provides for a food or feed product comprising or consisting of a plant part described herein. Preferably, the plant part is a lettuce leaf or a lettuce head or another plant part described herein. The food or feed product may be fresh or processed, e.g., dried, grinded, powdered, pickled, chopped, cooked, roasted, in a sauce, in a sandwich, pasted, puréed or concentrated, juiced, pickled, canned, steamed, boiled, fried, blanched and/or frozen, etc.

All documents (e.g., patent publications) are herein incorporated by reference in their entirety, including the following cited references:

Acquaah, Principles of Plant Genetics and Breeding, 2007, Blackwell Publishing, ISBN-13: 978-1-4051-3646-4
Martin et al. 2008, Australian Journal of Crop Science 1(2): 43-46
Nikolova V, Niemirowicz-Szczytt K (1996) Acta Soc Bot Pol 65:311-317
Parvathaneni et al., J. Crop Sci. Biotech. 2011 (March) 14 (1): 39-43.
Teng et al., HortScience. 1992, 27(9): 1030-1032
Teng et al. HortScience. 1993, 28(6): 669-1671 Vos et al. 1995, Nucleic Acid Research 23: 4407-4414
Vidaysky and Czosnek, (1998) Phytopathology 88(9): 910-4)
Zhang et al., Journal of Genetics and Breeding. 1992, 46(3): 287-290)
EP1197137
US20080222949
US20150126380
https://www.ams.usda.gov/sites/default/files/media/01-Lettuce %20ST-470-01%202015.pdf
http://www.upov.int/edocs/tgdocs/en/tg013.pdf
http://anrcatalog.ucanr.edu/pdf/7215.pdf
http://anrcatalog.ucanr.edu/pdf/7216.pdf

EXAMPLES

Development of NUN 09127 LTL

The inbred variety NUN 09127 LTL was developed from an initial cross between lettuce lines. The female and male ancestors were crossed to produce seeds. After the cross, progeny were self-pollinated or backcrossed, followed by pedigree selection and line selection. NUN 09127 LTL can be propagated by seeds or vegetatively, or by regeneration of a tissue culture. The seeds of NUN 09127 LTL can be grown to produce inbred plants and parts thereof (e.g., lettuce heads and leaves).

The Applicant concluded that NUN 09127 LTL is uniform and stable. This has been established through evaluation of horticultural characteristics. Several seed production events resulted in no observable deviation in genetic stability.

DEPOSIT INFORMATION

A total of 2500 seeds of the inbred variety NUN 09127 LTL have been deposited according to the Budapest Treaty by Nunhems B.V. on Jul. 22, 2020, at the NCIMB Ltd., Ferguson Building, Craibstone Estate, Bucksburn, Aberdeen AB21 9YA, United Kingdom (NCIMB). The deposit has been assigned NCIMB number 43644. A deposit of NUN 09127 LTL and of the parent line is also maintained at Nunhems B.V.

Access to the deposits will be available during the pendency of this application to persons determined by the Director of the U.S. Patent Office to be entitled thereto upon request. Subject to 37 C.F.R. § 1.808(b), all restrictions imposed by the depositor on the availability to the public of the deposited material will be irrevocably removed upon the granting of the patent. The deposit will be maintained for a period of 30 years, or 5 years after the most recent request, or for the enforceable life of the patent whichever is longer, and will be replaced if it ever becomes nonviable during that period. Applicant does not waive any rights granted under this patent on this application or under the Plant Variety Protection Act (7 U.S.C. § 2321 et seq.).

The most similar variety to NUN 09127 LTL is referred to as the Reference Variety, a variety from Nunhems B.V. with the commercial name Greenflash. Table 1 shows a comparison between NUN 09127 LTL and the Reference Variety Greenflash based on a trial in the USA during the trial season 2018. Trial location Acampo, Calif. (38.192873 N; 121.232637 W), harvesting date: Aug. 15, 2018.

A trial of at least 40 plants of each variety, from which at least 15 plants or plant parts were randomly selected, were used to measure characteristics. For numerical characteristics, averages are calculated. For non-numerical characteristics, the type/degree are determined. In Tables 1 and 2, USDA and Non-USDA descriptors of NUN 09127 LTL and the Reference Variety (commercial variety) Greenflash are listed, respectively, as measured in the performed trial.

In one aspect, the disclosure provides a plant having the physiological and morphological characteristics of NUN 09127 LTL as will be presented in Table 1 and/or 2.

TABLE 1

Objective description of NUN 09127 LTL and Reference Variety Greenflash (USDA descriptors); significant differences are highlighted in bold, where quantitative values are mentioned these are statistically significantly different between NUN 09127 LTL and Greenflash using an ANOVA Tukey test.

| USDA Descriptor | NUN 09127 LTL | Greenflash (Reference variety) |
|---|---|---|
| Plant type: 1 = Cutting/Leaf; 2 = Butterhead; 3 = Bibb; 4 = Cos or Romaine; 5 = Great Lakes Group; 6 = Vanguard Group; 7 = Salinas Group; 8 = Eastern (Ithaca) Group; 9 = Stem; 10 = Latin; 11 = Other (_) | 1 | 1 |
| Mature leaves (harvest mature outer leaves): Margin: | | |
| Incision depth (deepest penetration of margin): 1 = absent/shallow (Dark Green Boston), 2 = moderate (Vanguard), 3 = deep (Great Lakes 659) | 3 | 2 |
| Incision density: 3 = sparse, 5 = medium, 7 = dense, 9 = very dense | 5 | 9 |

TABLE 1-continued

Objective description of NUN 09127 LTL and Reference Variety Greenflash (USDA descriptors); significant differences are highlighted in bold, where quantitative values are mentioned these are statistically significantly different between NUN 09127 LTL and Greenflash using an ANOVA Tukey test.

| USDA Descriptor | NUN 09127 LTL | Greenflash (Reference variety) |
|---|---|---|
| Indentation (finest divisions of the margin): 1 = entire, 2 = shallowly dentate (Great Lake 65), 3 = deeply dentate (Great Lake 659); 4 = Crenate (Vanguard); 5 = Other (Specify) | 3 | 4 |
| Undulations of the apical margin: 1 = absent/slight (Dark Green Boston), 2 = moderate (Vanguard), 3 = strong (Great Lakes 659) | 3 | 2 |
| Green color: 1 = very light green, 2 = light green, 3 = medium green, 4 = dark green; 5 = Very Dark Green; 6 = other | 3 (RHS 137B) | 3 (RHS 137A) |
| Anthocyanin: | | |
| Distribution: 1 = absent; 2 = Margin Only (Big Boston); 3 = spotted (California Cream Butter); 4 = throughout (Prize Head); 5 = Other (_) | 1 | 1 |
| Concentration: 1 = light, 2 = moderate, 3 = intense | NA | NA |
| Size: 1 = small, 2 = medium, 3 = large | 2 | 2 |
| Glossiness: 1 = dull, 2 = moderate, 3 = glossy | 2 | 2 |
| Blistering: 1 = absent/slight, 2 = moderate, 3 = strong | 2 | 1 |
| Leaf thickness: 1 = thin, 2 = intermediate, 3 = thick | 3 | 1 |
| Trichomes; 1 = absent, 2 = present | 1 | 1 |
| Plant | | |
| Spread of frame leaves (cm) | 29 | 31.8 |
| Head diameter (market trimmed with single cap leaf) | NA | NA |
| Head shape: 1 = flattened, 2 = Slightly Flattened; 3 = Spherical; 4 = elongate, 5 = non-heading; 6 = other (_) | 5 | 5 |
| Head size class: 1 = small, 2 = medium, 3 = large | 2 | 2 |
| Head per carton | NA | NA |
| Head weight (gram) | 566 | 438 |
| Head firmness: 1 = loose, 2 = Moderate; 3 = Firm, 4 = very firm | 1 | 1 |
| Butt | | |
| Shape: 1 = slightly concave, 2 = flat, 3 = rounded; 4 = V-shaped | 3 | 3 |
| Midrib: 1 = Flattened, 2 = Moderately Raised, 3 = prominently raised | 3 | 2 |
| Core | | |
| Diameter at base of head (mm) | 22 | 17.6 |
| Ratio of head spread (frame leaves)/core diameter | 1.3 | 1.8 |
| Core height from base of head to apex (mm) | 28 (range 17.8 to 32.1) | 28.9 (range 20.2 to 40.1) |
| Maturity (earliness of harvest-mature head formation) | | |
| Summer (days) | 62 | 62 |
| Adaptation: | | |
| Primary regions of adaptation | West Coast 2, all seasons | West Coast 2, all seasons |
| Season: 0 = not tested, 1 = not adapted, 2 = adapted | | |
| Greenhouse: 0 = not tested, 1 = not adapted, 2 = adapted | 0 | 0 |
| Soil type: 1 = mineral, 2 = organic, 3 = both | 3 | 3 |

TABLE 2

Objective description of NUN 09127 LTL and Reference Variety Greenflash (Non USDA descriptors); significant differences are highlighted in bold, where quantitative values are mentioned these are statistically significantly different between NUN 09127 LTL and Greenflash using an ANOVA Tukey test.

| Non-USDA Descriptor | NUN 09127 LTL | Greenflash |
|---|---|---|
| Leaf length (mm) (harvest mature) | 170 | 171 |
| Leaf width (mm) (harvest mature) | 167 | 183 |
| Length/width ratio (harvest mature) | 1.0 | 0.93 |
| Plant height in cm (harvest mature) | 18.00 | 16.31 |

Table 1 and 2 contain typical values. Values may vary due to environment. Other values that are substantially equivalent are also within the scope of the disclosure. N.A.=not applicable; n.r.=not recorded.

The invention claimed is:

1. A plant, plant part, or seed of lettuce variety NUN 09127 LTL, wherein a representative sample of seed of said variety is deposited under Accession Number NCIMB 43644.

2. The plant part of claim 1, wherein the plant part is a leaf, a head, a pollen, an ovule, a fruit, a cutting, a flower, or a cell.

3. A seed that produces the plant of claim 1.

4. A seed grown on the plant of claim 1.

5. A lettuce plant of part thereof having all of the physiological and morphological characteristics of the plant of claim 1, when grown under the same environmental conditions.

6. A tissue or cell culture comprising cells of the plant of claim 1.

7. The tissue or cell culture according to claim 6, comprising cells or protoplasts derived from a plant part suitable for vegetative reproduction.

8. The tissue or cell culture according to claim 6, wherein the plant part is an embryo, a meristem, a cotyledon, a hypocotyl, a pollen, a leaf, a stem, a core, an anther, a root, a root tip, a pistil, a petiole, a flower, a fruit, a seed, or a stem.

9. A lettuce plant regenerated from the tissue or cell culture of claim 7, wherein the plant has all of the physiological and morphological characteristics of the plant of lettuce variety NUN 09127 LTL, when grown under the same environmental conditions, and wherein a representative sample of seed of lettuce variety NUN 09127 LTL is deposited under Accession Number NCIMB 43644.

10. A method of producing the plant of claim 1, the method comprising vegetatively propagating at least a part of the plant of variety NUN 09127 LTL, wherein a representative sample of seed of said variety is deposited under Accession Number NCIMB 43644.

11. The method of claim 10, wherein said vegetative propagation comprises regenerating a whole plant from said part of the plant of variety NUN 09127 LTL, wherein a representative sample of seed of said variety is deposited under Accession Number NCIMB 43644.

12. The method of claim 10, wherein said part is a cutting, a cell culture or a tissue culture.

13. A plant vegetatively propagated from the plant of claim 1, or a part thereof, wherein the vegetatively propagated plant has all of the physiological and morphological characteristics of the plant of lettuce variety NUN 09127 LTL, when grown under the same environmental conditions, and wherein a representative sample of seed of lettuce variety NUN 09127 LTL is deposited under Accession Number NCIMB 43644.

14. A method of producing a lettuce plant, the method comprising crossing the plant of claim 1 with a second lettuce plant at least once, and selecting a progeny plant from said crossing and allowing the progeny lettuce plant to form seed.

15. A first generation progeny of the plant of claim 1, obtained by crossing lettuce variety NUN 09127 LTL with itself or with another lettuce plant.

16. The first generation progeny plant of claim 15, wherein said progeny has all of the physiological and morphological characteristics of the plant of lettuce variety NUN 09127 LTL, wherein a representative sample of seed of said variety is deposited under Accession Number NCIMB 43644, when grown under the same environmental conditions.

17. A lettuce plant having all the physiological and morphological characteristics of the plant of claim 1, when grown under the same environmental conditions, wherein a representative sample of seed of lettuce variety NUN 09127 LTL is deposited under Accession Number NCIMB 43644, further comprising a transgene.

18. A plant of lettuce variety NUN 09127 LTL further comprising a transgene conferring a desired trait and otherwise, has all of the morphological and physiological characteristics of the plant of lettuce variety NUN 09127 LTL, wherein a representative sample of seed of said variety is deposited under Accession Number NCIMB 43644, when grown under the same environmental conditions, wherein the desired trait is yield, storage properties, color, male sterility, herbicide tolerance, insect tolerance, insect resistance, pest resistance, disease resistance, environmental stress tolerance, modified carbohydrate metabolism, or modified protein metabolism.

19. A method of making doubled haploid of lettuce variety NUN 09127 LTL, the method comprising making doubled haploid cells from haploids cells from the plant, plant part, or seed of claim 1 by chromosome doubling, wherein a representative sample of seed of lettuce variety NUN 09127 LTL is deposited under Accession Number NCIMB 43644.

20. A container comprising the plant, plant part, or seed of claim 1.

21. A food, a feed product, or a processed product comprising the plant part of claim 2.

22. A method of producing a lettuce head or a lettuce leaf, the method comprising growing the plant of claim 1 until it develops at least leaf or head, and collecting the leaf or head.

23. A method for inducing a mutation in the plant of claim 1, the method comprising:
   a. exposing the seed, plant, or plant part of lettuce variety NUN 09127 LTL to a mutagenic compound or to radiation, wherein a representative sample of seed of lettuce variety NUN 09127 LTL is deposited under Accession Number NCIMB 43644; and
   b. selecting seed, plant, plant part, or cell of lettuce variety NUN 09127 LTL having a mutation.

24. A method for collecting pollen of lettuce variety NUN 09127 LTL, the method comprising growing a plant of claim 1 until at least one flower contains pollen and collecting the pollen.

25. A method of producing a modified lettuce plant, wherein the method comprises mutating a lettuce plant or plant part of variety NUN 09127 LTL, wherein a representative sample of seed of lettuce variety NUN 09127 LTL is deposited under Accession Number NCIMB 43644.

26. A lettuce plant grown from the seed of claim 4.

* * * * *